United States Patent [19]  [11] Patent Number: 4,642,293
Chung  [45] Date of Patent: Feb. 10, 1987

[54] NOVEL HYBRIDOMA CELL LINE PRODUCING MONOCLONAL ANTIBODIES AGAINST LAMININ AND A PROCESS FOR THE PRODUCTION THEREOF

[75] Inventor: Albert E. Chung, Pittsburgh, Pa.

[73] Assignee: University of Pittsburgh, Pittsburgh, Pa.

[21] Appl. No.: 478,293

[22] Filed: Mar. 24, 1983

[51] Int. Cl.[4] ..................... C12N 5/00; C07K 15/04
[52] U.S. Cl. ..................................... 435/240; 435/68; 435/172.2; 435/7; 436/548
[58] Field of Search ................... 435/7, 68, 240, 241, 435/243, 172.2; 436/548

[56] References Cited

PUBLICATIONS

Chung et al. "Properties of a Basement-Membrane Related Glycoprotein Synthesized In Culture By a Mouse Embryonal Carcinoma-Derived Cell Line" 1979 Cell vol. 16, 277–287.
Fitch, John M. et al. Monoclonal Antibody Analysis of Ocular Basement Membranes During Development Developmental Biology 95 pp. 137–158 (1983).
Timpl, R. et al. "Laminin-A Glycoprotein From Basement Membranes Journal of Biological Chemistry" vol. 254, No. 19, pp. 9933–9937 (1979).
Springer, T. et al. "Monoclonal Xenogeneic Antibodies To Murine Cell Surface Antigens: Identification of Novel Leuckocyte . . . ". Differentiation Antigens Eur. J. Immunol vol. 8 pp. 539–551 (1978).
Melchers, F. et al., Ed. Lymphocyte Hybridomas Table 2 pp. XVIII–XXIII (Springer-Verlag Pub.) 1978.
Herbert, W. J. "Appendix 4 Laboratory Animal Techniques For Immunology" in Handbook of Experimental Immunology Weir, D. M. ed. pp. A4.1–A4.4 1979.

*Primary Examiner*—Charles F. Warren
*Assistant Examiner*—M. Moskowitz
*Attorney, Agent, or Firm*—Reed Smith Shaw & McClay

[57] ABSTRACT

The invention relates to a novel hybridoma continuous cell line that produces a monoclonal antibody of the IgG type to the glycoprotein GP-2, a subunit of the basement membrane component laminin. The hybridoma cell line is formed from a spleen cell from a Lewis rat, which has been immunized with a basement membrane antigen, fused with a mouse myeloma cell.

3 Claims, 7 Drawing Figures

Staining of MI536-B3 cells and extracellular matrix by 2AB1-IA10 and 3HA6-D6 monoclonal antibodies.

Staining of M1536-B3 cells and extracellular matrix by 2AB1-IA10 and 3HA6-D6 monoclonal antibodies.

Electrophoretic patterns of monoclonal antibodies separated on polyacrylamide gels.

Specificty of 2AB1-IA10 monoclonal antibody.

Reaction of 3HAG-DG with unglycosylated GP-2 precursors.

Differential staining of mouse kidney tubules by 2AB1-IA10 and 3HA6-D6 monoclonal antibodies.

Purification of laminin by 3HA6-D6 antibody affinity column.

Electrophoretic profiles of affinity purified laminin samples.

NOVEL HYBRIDOMA CELL LINE PRODUCING MONOCLONAL ANTIBODIES AGAINST LAMININ AND A PROCESS FOR THE PRODUCTION THEREOF

ACKNOWLEDGEMENT

The invention described herein was made during the course of work under Grant Nos. GM25690 and CA21246 of the National Institutes of Health.

FIELD OF THE INVENTION

The present invention relates to a hybridoma cell line in general, and specifically, to a hybridoma cell line, and a method for its production, that produces monoclonal antibodies against the basement membrane component laminin and more specifically against glycoprotein GP-2, a subunit of laminin.

BACKGROUND OF THE INVENTION

Basement membranes are complex, extracellular matrices that play a role in vital functions, such as embryogenesis, tissue organization, vascular architecture and kidney glomerular filtration. The major components of basement membranes that have been identified include Type IV collagen (P. Bornstein et al., *Annu. Rev. Biochem.* 49:957 (1980), and N. A. Kefalides, *Biology and Chemistry of Basement Membranes* (1978), Academic Press, New York); fibronectin (E. Ruoslahti et al., *Coll. Res.* 1:95 (1981)); the glycoprotein CP-1 (A. E. Chung et al., *Biochem. Biophys. Res. Commun.* 79:879 (1977)); the glycoprotein CP-2 (A. E. Chung et al., *Cell* 16:277 (1979)); laminin (J. M. Foidart et al., *Lab. Invest.* 42:336 (1980)); heparan sulfate, (Y. S. Kanwar et al., *Proc. Natl. Acad. Sci. U.S.A.* 76:1303,76:4493 (1979); and entactin (B. Carlin et al., *J. Biol. Chem.* 256:5209 (1981) and B. L. Bender et al., *Am. J. Pathol.* 103:419 (1981). It would appear that the glycoproteins GP-1 and GP-2 form the laminin complex. (R. Timpl et al., *J. Biol. Chem.* 254:9933 (1979)).

Basement membranes are found at the base of epithelial and endothelial cells and at the interface between cells and the connective tissue matrices. They are synthesized by a variety of cells including the endothelium of the capillaries, the epithelium of the kidney glomerulus and tubule, the parietal endoderm of the yolk sac, the epithelial cells of lens capsule, and the epithelium of glandular, respiratory and gastrointestinal tissues. The membranes undergo morphological and presumably functional changes under a variety of pathological states such as systemic lupus erythematosus, diabetes mellitus, Goodpasture's syndrome, and post-streptococcal glomerulonephritis (N. A. Kefalides, *J. Invest. Dermatol.* 65:85 (1975)). In these diseases, different tissues are affected e.g. in diabetes mellitus the basement membranes of both the kidney glomerulus and the capillaries of muscle are affected. The variety of functions of basement membranes suggest the possibility of microheterogeneity of the macromolecular components and diversity in their organization. Among the functions which have been ascribed to basement membranes are (a) filtration, notably of plasma in the kidney glomeruli, (b) organization of tissues and organs by delineation of boundaries between groups of cells and (c) provision of a matrix for cell adhesion. (M. G. Farquhar, *Biology and Chemistry of Basement Membranes* (1978), pp. 43-80, Academic Press, New York).

The precise roles of these macromolecules within the basement membrane are not understood in detail at present. Fibronectin has been shown to have effects on cell morphology (L. B. Chen et al., *Cell* 14:377 (1978)), adhesion (I. U. Ali et al., *Cell* 11:115 (1977)) and contact inhibition (K. M. Yamada et al., *Proc. Nat'l Acad. Sci. U.S.* 73:1217 (1976)). Heparan sulfate has been suggested to play a key role in glomerular filtration by virtue of its negative charge (Y. S. Kanwar et al., *Proc. Nat'l. Acad. Sci. U.S.* 76:1303 (1979)). It is believed that the sulfated glycoprotein entactin may play a similar role. Several lines of evidence also indicate that glycoprotein GP-2 (A. E. Chung et al., *Cell* 16:277 (1979)), entactin (B. Carlin et al., *J. Biol. Chem.* 256:5209 (1981) and B. L. Bender et al., *Amer. J. Pathol.* 103:419 (1981)) and laminin are involved in cell adhesion and early embryogenesis in the mouse (P. Ekblom et al., *Proc. Nat'l. Acad. Sci. U.S.* 77:485 (1980)).

There still exist voids in the understanding of the structure and biosynthesis of basement membranes. In an effort to better understand the structure and biosynthesis of basement membranes and its components, and to better correlate structural organization with function, hybridoma cell lines have been developed that produce monoclonal antibodies directed against the basement membrane components.

Although hybridoma cell lines that produce monoclonal antibodies, such as antibodies to hepatitis virus, are known in the prior art, e.g. the cell lines disclosed in U.S. Pat. No. 4,271,145, hydriboma cell lines that produce monoclonal antibodies against laminin are unknown.

A hydridoma cell line has now been developed that provides an unlimited supply of a unique and unchanging antibody that is directed against the basement membrane component laminin, or more specifically the glycoprotein GP-2, a subunit of the laminin complex. This novel cell line and the resulting antibody can be used for medical diagnoses, studies on development of animal embryos and a variety of research activities involving the structure and function of basement membranes.

SUMMARY OF THE INVENTION

The subject invention relates to a novel hybrid composition, and a process for the production thereof, comprising a continuous cell line that produces a monoclonal antibody to the basement membrane component laminin further comprising a cell hybrid of a lymphocyte cell of an animal immunized with a basement membrane antigen fused with a myeloma cell. In a preferred embodiment, the hybridoma cell line produces a monoclonal antibody to the glycoprotein GP-2, a subunit of laminin, and comprises a cell hybrid of spleen cell of a Lewis rat immunized with a basement membrane antigen fused with a mouse myeloma cell. In a further embodiment of the invention, the composition includes a culture medium for the hybridoma cell line.

The resulting hybridoma can be successfully cloned and produces a monoclonal antibody to individual antigenic determinants unique to the laminin complex.

DETAILED DESCRIPTION OF THE INVENTION

Figure 1:
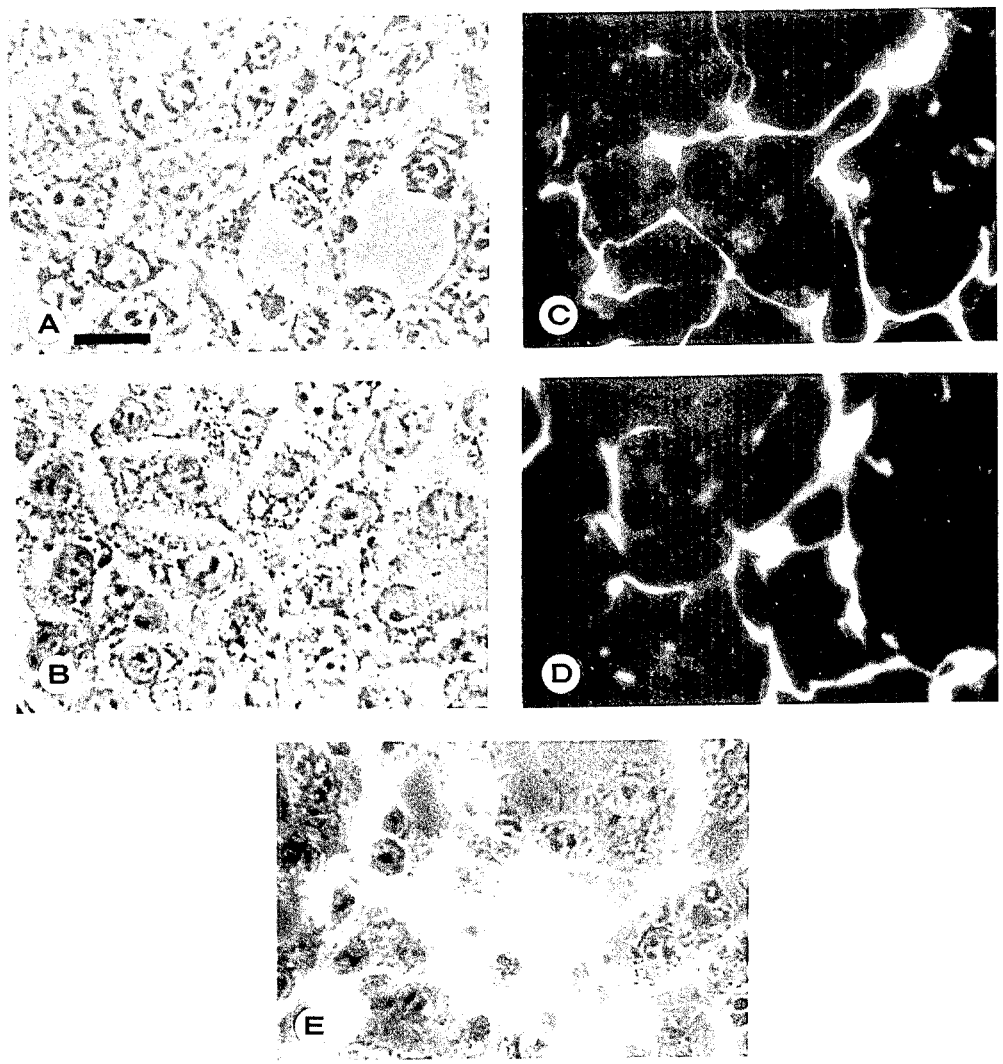
FIG. 1 is a micrograph displaying staining of an extracellular matrix from M1536-B3 cells by 2AB1-IA10 and 3HA6-D6 monoclonal antibody.

In accordance with the invention, a hybridoma cell is constructed using the procedure described by G. Kohler and C. Milstein, *Nature* 256:495 (1975), the disclosure of which is incorporated herein by reference. The technique involves the immunization of an animal with an antigen and the subsequent harvesting and isolation of the cells of interest. The isolated animal cells are immortalized by chemically fusing the antibody producing cell with a myeloma or cancer cell that can grow indefinitely in vitro. The resulting hybrid cell inherits the antibody-producing ability of the stimulated cell and the immortality of the myeloma or cancer cell. Cells that produce the antibodies are identified by screening techniques and then cloned and propagated. The antibodies produced by these cells are of unchanging chemical structure directed against a single antigenic site on the antigen.

More specifically, host animals, preferably Lewis rats, are immunized with an extracellular matrix basement membrane-like preparation, such as that isolated from M1536-B3 cultures and described by A. E. Chung et al in *Biochem. Biophys. Research Commun.* 79:859 (1977), the disclosure of which is incorporated herein by reference. Alternatively, laminin, which is commercially available from Bethesda Laboratories, Bethesda, Md., may be used in place of the basement membrane preparation. The immunization schedule consists of injecting a suspension of basement membrane-like extracelluar matrix at ten day intervals for two months and a daily injection each day for five days prior to sacrifice of the animals. Serum is taken from the animals at intervals during the immunization schedule. The serum is tested for the presence of antibodies against basement membrane components on M1536-B3 cells as described by A. E. Chung et al. in *Cell* 16:277 (1979), the disclosure of which is incorporated herein by reference. After the final steps in the immunization schedule, the spleen is removed from the host animal, and the spleen cells are isolated. The isolated spleen cells are treated with 0.17M $NH_4Cl$ and fused with a myeloma cell line, preferably myeloma cell line Sp2/0-Ag14, disclosed by M. Shulman et al. in *Nature* 276:269 (1978), the diclosure of which is incorporated herein by reference, and available from the Salk Institute, La Jolla, Calif., according to the protocol described by R. H. Kennett in *Monoclonal Antibodies* (1980), pp. 365–371, Plenum Press, New York, the disclosure of which is incorporated herein by reference. A ratio of spleen cells to Sp 2/0-Ag14 of 10:1 is used and a suitable fusing agent, such as Polyethyleneglycol 4000. The fusion mixture is next distributed into 4, 24 well microtiter plates in a suitable growth medium such as a mixture of α-MEM (Modified Eagle's Medium), 10% activated horse serum and HAT (hypoxanthine 0.1 mM, aminopterin 0.4 uM, thymidine 16 mM, and the cells allowed to propagate. The growth medium in each well is tested for the presence of antibody by the method described by A. E. Chung et al in *Cell* 16:277 (1979). Those cells in wells containing antibody are transferred and further propagated.

Hybridomas which synthesize and secrete monoclonal antibodies directed toward the basement membrane component laminin then are cultured to establish continuously proliferating cell lines with relatively stable genetic properties. The cell lines or clones are propagated in tissue culture where they continue to synthesize and secrete antibody to the laminin complex. Antibody is then recovered from the tissue culture cells or from the ascites fluids by known procedures, such as conventional precipitation, ion exchange or affinity chromatography.

The hybridoma cell line obtained by the present invention is capable of producing a monoclonal antibody of the IgG type directed against the laminin complex and more particularly the GP-2 subunit of laminin. A deposit of this hybridoma cell line culture identified internally as cell line 2AB1-IA10 is on deposit with the American Type Culture Collection (ATCC) and is assigned ATCC Accession Number HB8210.

EXPERIMENTAL STUDIES

The hybridoma cell line of the present invention which produces monoclonal antibodies was produced and characterized using the following protocol:

MATERIALS AND METHODS

Cell Cultures. The mouse endodermal cell line M1536-B3 was isolated and grown as previously described by A. E. Chung et al, *Cancer Res.* 37:2072 (1977), the disclosure of which is incorporated herein by reference. These cells produce an extracellular matrix and are used as the target cells in initial screening procedures. For screening, cells were seeded on 10-well microslide culture chambers at $2 \times 10^4$ cells/well in 0.2 ml of Dulbecco's Modified Eagle's Medium (DMEM) (GIBCO, New York, NY) containing 10% fetal calf serum and incubated at 37° C. in humidified 10% $CO_2$ for 48 hours. The non-secreting mouse myeloma SP2/0-Ag14 was isolated by the method disclosed by Shulman et al. in *Nature* 276:269 (1978) and obtained from the Salk Institute, La Jolla, CA. These cells and the hybridomas produced from them were grown in α-MEM (GIBCO, Grand Island, N.Y.) containing 10% heat-inactivated horse serum.

Basement Membrane Components. Extracellular basement matrix from M1536-B3 cultures was isolated as described by A. E. Chung et al., *Biochem. Biophys. Res. Commun.* 79:859 (1977). The laminin subunits GP-1 and GP-2, and entactin A and B are obtained by preparative polyacrylamide gel electrophoresis as previously described by B. Carlin et al., *J. Biol. Chem.* 256:5209 (1981), the disclosure of which is incorporated herein by reference, and A. E. Chung et al. *Cell* 16:277 (1979). The extracellular matrix consists almost exclusively of laminin, entactin A, and entactin B. The individual polypeptide chains are separated, after denaturation and reduction in sample buffer, by electrophoresis on polyacrylamide slab gels in the presence of sodium dodecyl sulfate according to the procedures descirbed by U. K. Laemmli, *Nature* 227:680 (1970), the disclosure of which is incorporated herein by reference. The separated matrix components were transferred to nitrocellulose filters by the electrophoretic blotting technique of H. Towbin et al., *Proc. Nat'l. Acad. Sci. U.S.A.* 76:4350 (1979), the disclosure of which is incorporated herein by reference, and used to determine antibody specificity.

Immunochemical Reagents. Fluorescein isothiocyanate (FITC) and rhodamine-conjugated rabbit anti-rat IgG antibodies were obtained from Cappel Laboratories, Cochranville, PA. Horse radish peroxidase-conjugated (HPO) rabbit anti-rat IgG antibody was purchased from Accurate Chemicals, Westbury, N.Y. The chromogonic substrate 3-amino-9-ethylcarbazole was obtained from Sigma Chemical Co., St. Louis, MO.

Detection of Antibody. The presence of rat anti-laminin antibodies was initially assessed by indirect immunofluorescence using the procedure described by A. H. Coons in *General Cytochemical Methods* (Danielli, J. F., ed.)(1958), pp. 339–435, Academic Press, New York, the disclosure of which is incorporated herein by reference. M1536-B3 cells grown in microslide chambers were fixed with ethanol, washed with phosphate buffered saline (PBS) and treated with the α-MEM growth medium (GIBCO, New York, N.Y.) from the hybridoma cultures. The cell layers were washed with PBS and stained with the secondary fluorescent antibody. After thorough washing of the cell layers the microslide chamber was dismantled, and the slide mounted in 0.1M glycine buffer, pH 9, containing 50% glycerol (v/v). Fluorescence was detected with a Zeiss microscope equipped for epi-illumination.

Determination of Antibody Specificity. Antibody specificity was determined by indirect immunoperoxidase staining. Matrix components separated on polyacrylamide gels and blotted into nitrocellulose filters were stained with the monoclonal antibody and then with HPO conjugated rabbit anti-rat IgG antibodies as described by H. Towbin et al., *Proc. Nat'l. Acad. Sci. U.S.A.* 76:4350 (1979). The bound secondary antibody was detected with 3-amino-9-ethylcarbazole/$H_2O_2$ reagent according to Graham et al., *J. Histochem. Cytochem.* 13:150 (1965), the disclosure of which is incorporated herein by reference.

Construction and isolation of Hybridomas. Lewis rat pups were immunized by intramuscular injection (at 10 day intervals), of 250 ug samples of matrix proteins from M1535-B3 cultures (antigen) suspended in complete Freund's adjuvant, although between about 150 and 300 ug, more preferably about 250 and 300 ug, is a suitable dosage. Blood samples were obtained at intervals and the serum tested for the presence of antibodies. When strong positive reactions were obtained, the rats were injected with 500 ug of antigen on three successive days, although between about 400 and 600 ug, more preferably about 500 and 600 ug, is a suitable dosage. Seventy-two hours after the final injection, the rats were sacrificed. Spleen cells were obtained and fused with mouse SP2/0-Ag14 myeloma cells according to the protocol described by Kennett in *Monoclonal Antibodies* (1980) (Kennett, R. H., McKearn, T. J., and Bechtol, K. B., eds.) pp. 365–371, Plenum Press, New York. The fusion mixture was distributed into 4, 24-well microtiter plates in medium consisting of α-MEM, 10% heat inactivated horse serum, and HAT (hypoxanthine 0.1 mM, aminopterin 0.4 uM, thymidine 16 mM). The growth medium for each well was screened for the presence of antibody, and positive cultures were expanded and cloned. Cloning was accomplished either by removal of single cells under a dissecting microscope with a micropipette and transferring to 96 well plates, or by limiting dilution. Positive cultures were recloned until stable antibody producing lines were obtained.

Preparation and Purification of Monoclonal Antibodies. Monoclonal antibodies were obtained from hybridoma growth medium or from ascites fluids generated by injecting the hybridomas into pristane-primed nude mice. Growth medium, either serum-free or containing 10% horse serum was made 50% saturated with ammonium sulfate to precipitate the antibody. The precipitated antibody was redissolved in PBS and dialyzed overnight against 100–200 volumes of PBS. Ascites fluids were purified on DEAE-cellulose columns as described by J. S. Garvey et al. in *Methods in Immunology* (1977), pp. 223–226, W. A. Benjamin, London, the disclosure of which is incorporated herein by reference. Samples of purified ascites antibodies were analyzed on polyacrylamide gels as described by U. K. Laemmli in *Nature* 227:680 (1970) and G. Fairbanks et al. in *Biochemistry* 10:2607 (1971), the disclosure of which is incorporated herein by reference. Replicas of the reduced antibodies, separated on polyacrylamide gels, were obtained by electrophoretic transfer to nitrocellulose paper. The replicas were stained with rabbit anti-rat IgG antibodies and visualized with peroxidase-conjugated swine anti-rabbit IgG antibodies to determine the origin of the immunoglobulin chains.

Determination of Heavy Chain Class. The nature of the heavy chain of the monoclonal antibodies were determined by Ouchterlony double diffusion as described by J. S. Garvey et al. in *Methods in Immunology* (1977), pp. 313–321, W. A. Benjamin, London. Chain specific anti-rat heavy chain antibodies were used as the precipitating agent.

Preparation and Staining of Tissues. Fresh tissues, both mouse and human, were used without fixation. Tissues were placed in plastic molds filled with chemical fixative OCT (Lab-Tec Products, Napierville, IL) and snap-frozen in isopentane cooled in liquid nitrogen. Cryostat sections were cut as soon as possible at 3–5 microns and picked up on albuminized slides, then air-dried at −20° C. overnight. After light fixation in cold acetone, 4° C. for 10 minutes, the tissues were rinsed in PBS pH 7.2. Endogenous biotin-avidin binding was determined for each tissue and where needed, blocked using successive incubations in avidin (0.05%, Sigma followed by biotin (0.005%, Sigma), according to the method of G. S. Wood et. al. in *J. Histochem.* 29:1196 (1981), the disclosure of which is incorporated herein by reference. Monoclonal rat antibodies were applied to the tissues for 1 hour at room temperature. Normal rat serum was substituted for primary antibody as a negative control. After a PBS wash, biotinylated anti-rat serum (1:100) (obtained from Vector Laboratories, Inc., Burlingame, CA) was applied to the tissues for ½ hour at room temperature, followed by a wash in PBS and incubation with avidin-biotin complex (also obtained from Vector Laboratories, Inc., Burlingame CA) for 1 hour at room temperature using the procedure disclosed by S.M. Hsu et al. in *Am. J. Clin. Pathol.* 75:734 1981, the disclosure of which is incorporated herein by reference. Optimal dilutions of primary antibody were established using a checkerboard method of titration against the other antisera.

0.5 mg/ml of diaminobenzidine (obtained from Polyscience, Worthington, PA) with 0.01% $H_2O_2$, in Tris-Saline (Fisher THAM (trishydroxyaminomethane)) pH 7.6 was used as the chromogen. Tissues were darkened in 0.5% CuSO$_4$, dehydrated, cleared and mounted without counterstain or with brief exposure to hematoxylin only.

Construction of Affinity Columns with Monoclonal Antibodies. Monoclonal antibodies purified on DEAE-cellulose columns were derivatized with N-hydroxysuccinimidobiotin (obtained from Pierce Chemical Co., Rockford, IL) as described by H. Heitzman et al. in *Proc. Nat'l. Acad. Sci. U.S.A.* 71:3537 (1974), the disclosure of which is incorporated herein by reference. Approximately 10 mg of antibody in 1 ml of 0.1M NaHCO$_3$ was reacted with 1.2 mg of the derivatizing agent in 0.1 ml of N,N-dimethylformamide for 60 min. at room temperature. The biotinylated antibody was separated from unreacted reagent and low molecular weight products on a Sephadex G-25 column equilibrated with 0.9% NaCl. The biotinylated antibody was bound by passing it through a column packed with Sepharose-avidin (Vector Laboratories, Inc. Burlingame, CA). The affinity column containing the immobilized antibody was thoroughly washed with PBS and 6M urea in PBS.

RESULTS AND PROPERTIES OF THE MONOCLONAL ANTIBODIES PRODUCED BY THE CLONED HYBRIDOMAS

Production of Hybridomas and Characterization of Monoclonal Antibody Species. Two stable rat x mouse hybridoma lines were obtained from two independent fusion experiments with rat spleen and mouse myeloma cells. These stable cell lines were internally designated 2AB1-IA10 and 3HA6-D6. The growth medium from these lines and their subclones reacted with the extracellular matrix of the mouse endoderm line M1536-B3 as shown for 2AB1-IA10 in FIG. 1. The cells shown in panel A (phase contrast) were stained with 3HA6-D6 and photographed for fluorescence as shown in panel C. The cells in panel B were stained with 2AB1-IA10, the fluorescent pattern obtained is shown in panel D. In panel E the film was double exposed, under phase and fluorescent illumination. This demonstrates the relationship of laminin to the cells, the anti-body used was 3HA6-D6. The bar in panel A represents 20 um. Antibodies obtained from the culture media of 2AB1-IA10 and 3HA6-D6 were tested by Ouchterlony double diffusion against rabbit antisera specific for the heavy chains of rat immunoglobins.

These experiments demonstrated that both hybridoma cell lines produced rat IgG antibodies, the heavy chain of 2AB1-IA10 being of the G2b type and the heavy chain of 3HA6-D6 being of the G2a type.

Figure 2:
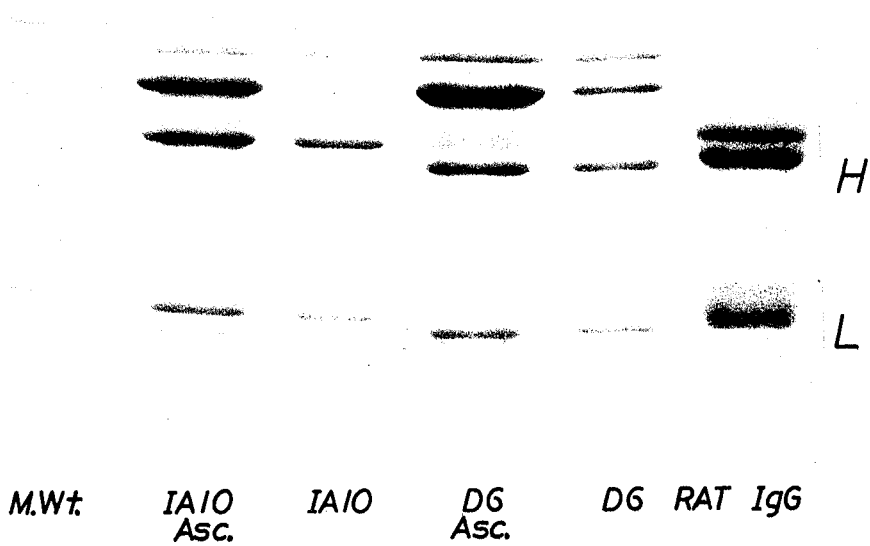
FIG. 2 depicts electrophoretic patterns of monoclonal antibodies separated on polyacryamide gels.

The ascites fluids obtained by injection of pristane-primed nude mice yielded antibodies of high titer that gave positive reactions with extracellular matrix at dilutions greater than 1:2000. These ascites fluids were purified on DEAE-cellulose columns and the IgG fractions analyzed by electrophoresis on polyacrylamide gels. The results are shown in FIG. 2. The molecular weight markers are shown in lane 1. The 2AB1-IA10 ascites fluid is shown in lane 2 and the purified 2AB1-IA10 antibody is shown in lane 3. As may be seen it contains only a minor contaminant in the 80K dalton range. The 3HA6-D6 ascites fluid is shown in lane 4 and the purified antibody in lane 5. This sample contained some albumin and the 80K protein. Rat immunoglobin G is shown in lane 6. Both the heavy and light chains of the monoclonal exhibited distinct electrophoretic mobilities. From the relative mobilities of the light chains, the 2AB1 antibody appears to be IgG2b (lambda) and the 3HA6-D6 IgG2a (kappa). The rat origin of the heavy and light chains was confirmed by electrophoretic blotting of the proteins to nitrocellulose paper and staining the blot with horse radish peroxidase conjugated rabbit anti-rat IgG antibodies.

Figure 3:
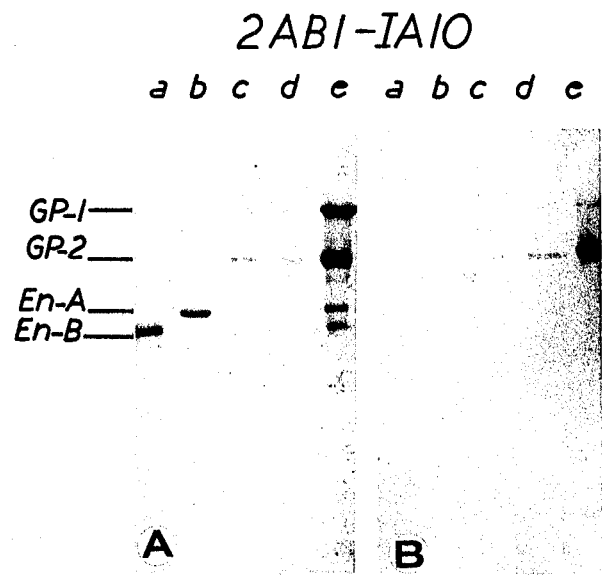
FIG. 3 depicts the specificity of 2AB1-IA10 monoclonal antibody.

Specificity of Monoclonal Antibody. The specificity of the monoclonal antibodies was tested on transfers of extracellular matrix proteins to nitrocellulose paper. The extracellular matrix consisted of GP-1, GP-2, entactins A and B and other minor proteins species. FIG. 3 displays duplicate transfers of matrix proteins. Panel A was stained with amido black and contained entactin B, lane a; entactin A, lane b; a purified mixture of GP-1 and GP-2, lanes c and d; and extracellular matrix from M1535-B3 cells, lane e. Panel B was stained with 2AB1-IA10 monoclonal antibody. It is clear that 2AB1-IA10 reacted with GP-2 and a sharp band that migrated in the GP-1 region. There was no reaction with entactin A or B. It may also be seen that the antibody did not react with purified GP-1 which suggested that the sharp band in the GP-1 region could be a dimeric form of GP-2. Identical results were obtained with the 3HA6-D6 monoclonal antibody. It is, therefore, concluded that both monoclonal antibodies recognized antigenic determinants on the GP-2 subunit of laminin.

Figure 4:
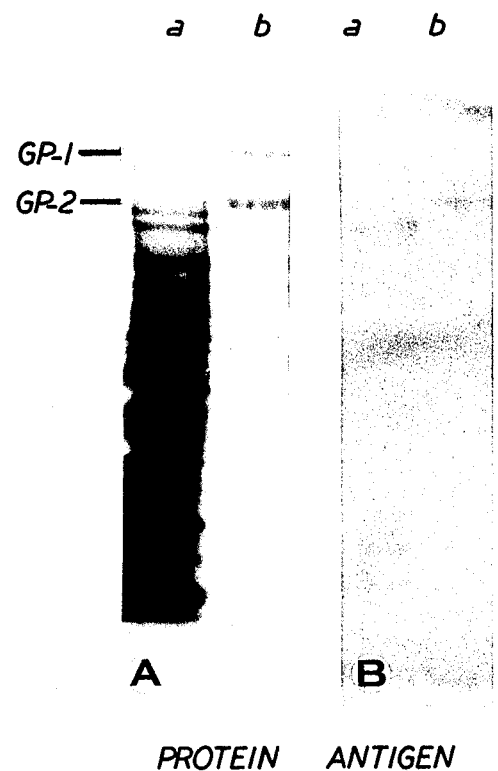
FIG. 4 represents the reaction of 3HA6-D6 monoclonal antibody with unglycosylated GP-2 percursors.

Experiments were carried out to determine if the antigenic determinant resided in the carbohydrate moiety of GP-2. It has been found that tunicamycin inhibited the glycosylation of laminin in M1536-B3 cells and that the unglycosylated precursors have molecular weights of approximately 195,000 and 182,000. Staining of the electrophoretic blots of the unglycosylated precursors demonstrated that the 182,000 dalton band reacted with the 3HA6-D6 antibody as shown in FIG. 4. Panels A and B are duplicate blots on nitrocellulose paper of samples separated on polyacrylamide gels. Panel A was stained with amido black and panel B with the antibody. Lane a contained an extract of M1536-B3 cells treated in culture for 6 hr. with 5 ug/ml tunicamycin. The two protein bands just below GP-2 are its unglycosylated precursors of apparent molecular weights 195,000 and 182,000. Lane b contained a sample of M1536-B3 extracellular matrix proteins. The antibody appeared to recognize some low molecular weight components (Panel B, lane a) that could be degradation products of GP-2. Similar results were obtained with the 2AB1-IA10 antibody. These data suggest that the monoclonal antibodies recognized antigenic determinants in the polypeptide backbone rather than the oligosaccharide chains.

Figure 5:
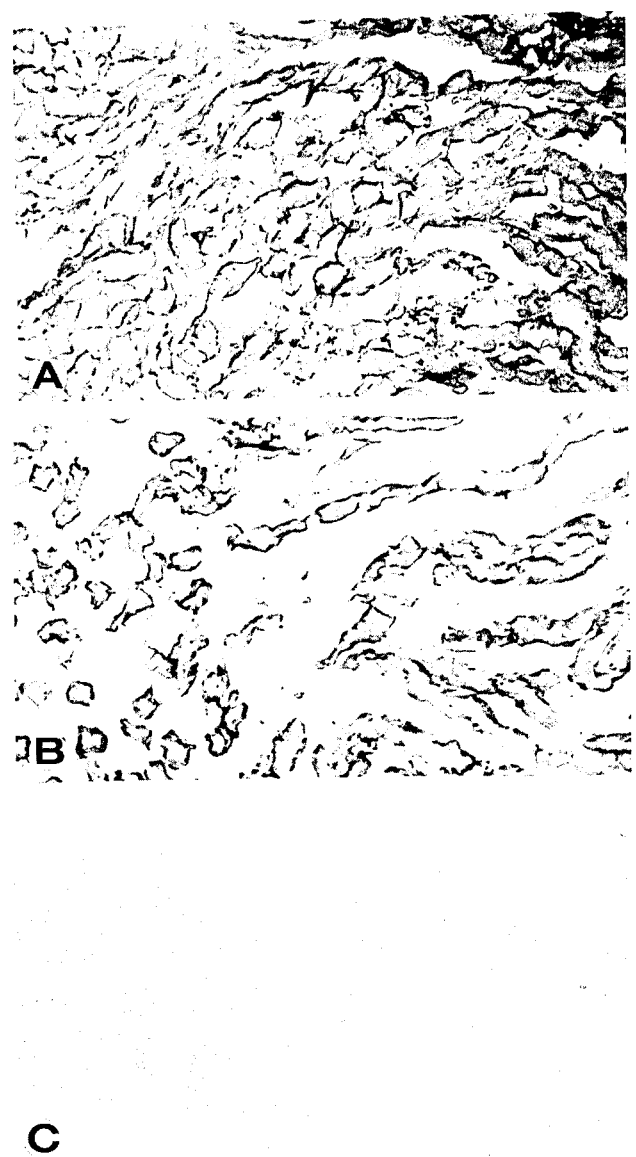
FIG. 5 is a micrograph displaying differential staining of mouse kidney tubules by 2AB1-IA10 and 3HA6-D6 monoclonal antibodies.

Recognition of Antigenic Determinants in Basement Membranes of Tissues. The monoclonal antibodies were used to stain the basement membranes of frozen human and mouse tissue sections. The 3HA6-D6 monoclonal antibody did not stain any of the several human basement membranes tested. However, the antibody stained the lobular basement membranes of mouse thymus and a select population of kidney tubular basement membranes. The staining patterns of mouse kidney tubular basement membranes by the 3HA6-D6 and 2AB1-IA10 antibodies are compared in FIG. 5. These kidney sections were obtained from the same region of the same kidney. The dramatic selectivity of the 3HA6-D6 is obvious from panel B. This is in sharp contrast to the staining pattern obtained with the 2AB1-IA10 antibody shown in Panel A, where all the basements membranes were stained. Panel C was stained with normal rat serum at a dilution of 100. In contrast to the selectivity of the 3HA6-D6 monoclonal antibody, the 2AB1-IA10 antibody surprisingly exhibited a much broader specificity. This antibody recognized antigenic determinants in a wide cross section of basement membranes from both mouse and human tissues. Table 1 below summarizes the results obtained with the 2AB1-IA10 antibody. The specificity of the 2AB1-IA10 antibody parallels that obtained with rabbit polyclonal anti-GP-2 antiserum.

TABLE I

Basement Membrane Staining With 2AB1-IA10 Monoclonal Antibody

| SPECIES | TISSUE | STAINING |
|---|---|---|
| Mouse | Kidney: tubular and glomerular | Positive |
| | Skin: epithelial and vascular | Positive |
| | Thymus: lobular and vascular | Positive |
| Human | Kidney: glomerular | Negative |
| | Kidney: tubular | Positive |
| | Liver: bile duct, vascular | Positive |
| | Large Intestine: epithelial vascular, smooth muscle, nerve | Positive |
| | Renal Cell Carcinoma: vascular and stromal | Positive |
| | Yolk Sac Tumor: vascular | Positive |
| | Skin: epidermal, vascular, nerve, fat cells | Positive |
| | Heart: vascular | Positive |
| | Thyroid: epithelial and vascular | Positive |
| | Striated muscle: vascular and endothelial | Positive |
| | Spleen: vascular and smooth muscle of white pulp | Positive |
| | Spleen: sinuses | Negative |
| | Neuroblastoma | Negative |
| | Breast: epithelial, fat, vascular | Negative |
| | Hemangioma: vascular and nerve sheath | Positive |

Figure 6:
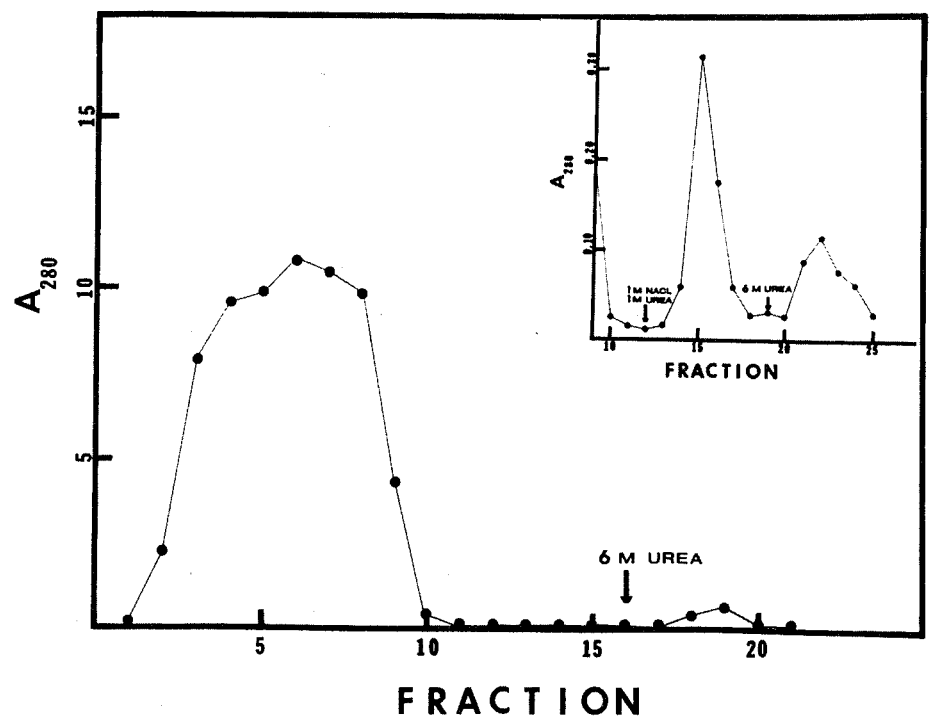
FIG. 6 is a graphical representation of purification of laminin by 3HA6-D6 antibody affinity column.

Purification of Laminin by Affinity Columns Constructed with Monoclonal Antibodies. Affinity columns constructed as described above were used to isolate laminin from the culture medium of M1536-B3 cells. The columns contained approximately 1 mg. of antibody/ml of packed gel. Aliquots of the 50% ammonium sulfate fraction of culture medium were subjected to affinity chromatography. The elution profile of a typical experiment with a 3HA6-D6 antibody column is shown in FIG. 6. Twenty ml of concentrated M1536-B3 culture medium containing 248 $A_{280}$ units of protein were passed through the 5 ml affinity column in PBS. The column was then eluted with 6M urea in PBS as indicated. Samples, 3 ml each, were collected and monitored for absorbance at 280 mm. The elution profile is shown. In the inset, the elution profile is shown for a separate experiment in which the elution of adsorbed proteins was carried out first with 1M NaCl-1M urea in PBS and then with 6M urea in PBS. The flow rate of the column was 0.5 ml/min. Most of the protein in the applied sample was not adsorbed by the column and was eluted with the starting buffer. A small protein peak was subsequently eluted with 6M urea dissolved in PBS, and as below, this peak contained laminin. The adsorbed protein could be further fractionated as shown in the inset by elution with 1M sodium chloride-1M urea in PBS followed by elution with 6M urea in PBS. The eluted fractions were concentrated by precipitation with ammonium sulfate at 50% saturation and analyzed on polyacrylamide gels after reduction with 5% 2-mercaptoethanol and denaturation in 2% sodium dodecyl sulfate.

Figure 7:
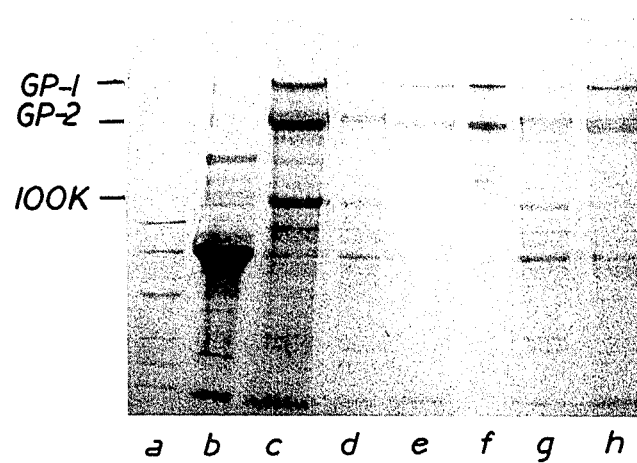
FIG. 7 displays the electrophoretic profiles of affinity purified laminin samples.

The Coomassie Blue stained gel is presented in FIG. 7. The crude sample applied to the column in lane b may be compared with the sample eluted with 6M urea shown in lane c. There is a dramatic increase in the GP-1 and GP-2 bands of laminin, and also an unidentified 100K dalton band. The fractions eluted as shown in the inset of FIG. 6 are shown in lanes d and e. The 1M NaCl-1M urea fraction contained a doublet of slightly larger apparent molecular weight than GP-2, the 100K band, several other components, but very little laminin. The second peak consisted almost exclusively of GP-1 and GP-2 with some entactin A. These results demonstrate the potential use of the affinity column to isolate laminin in an almost homogeneous state from a crude solution. In lanes g and h, the adsorbed proteins were eluted first with 1M NaCl in PBS (lane g) and then with 6M urea in PBS (lane h). This protocol was not as effective for obtaining purified laminin as that described above. Lane a contains molecular weight markers and lane f, M1536-B3 extracellular matrix. The molecular weight markers consisted of: myosin, 200,000; galactosidase, 116,500; phosphorylase b, 94,000; bovine serum albumin, 68,000; ovalbumin, 43,000; carbonic anhydrase, 30,000; soybean trypsin inhibitor 21,000; and lysozyme 14,300.

As the above experiments and data reveal, the two monoclonal antibodies exhibit significantly different staining patterns. The monoclonal antibody from hybridoma cell line 2AB1-IA10 stained mouse glomerular, tubular basement membranes and human tubular basement membranes, while the monoclonal antibody from hybridoma cell line 3HA6-D6 stained only a specific population of mouse tubular basement membranes. These results clearly indicate that in the same organ of different species different antigenic determinants to laminin are recognized, and further suggest that laminin molecules are species specific. The differential staining is not due to variations in oligosaccharide structures since the monoclonal antibodies react with the unglycosylated precursors of GP-2. The relatively broad staining specificity of the 2AB1-IA10 monoclonal antibody, as compared to the 3HA6-D6 monoclonal antibody, for mouse and human basement membranes, is surprising and unexpected.

Such broad character staining specificity exhibited by the monoclonal antibody produced from hybridoma cell line 2AB1-IA10 suggests its use in a variety of applications including the following research applications:

examination of the role of laminin in embryogenesis of humans and animals;

examination of the role of laminin in nerve-muscle interactions;

examination of the role of laminin in liver regeneration and damage;

examination of the interaction of cells and basement membrane;

studies on the role of laminin in cell adhesion and metastasis;

studies on the process of induction; and isolation of laminin;

and the following medical applications:

detection of metastatic cells;

studies on the process of wound healing;

studies on changes in liver cirrhosis and liver regeneration;

studies on changes in kidney, heart, lung, spleen basal lamina from diseases; and studies as a possible agent for blocking trypanosome infections such as African sleeping sickness.

What is claimed is:

1. The composition assigned ATCC Accession Number HB 8210 comprising a hybrid continuous cell line that produces a monoclonal antibody of the IgG type to the glycoprotein GP-2, a subunit of the basement membrane component laminin, said cell line comprising a spleen cell from a Lewis rat, immunized with a M-1536-B3 basement membrane component that contains the GP-2 antigen, fused with a mouse SP2/0-Ag14 myeloma cell.

2. The composition of claim 1 wherein the composition includes a culture medium for said hybrid continuous cell line.

3. The composition of claim 2 wherein the culture medium contains hypoxanthine-aminopterinthymidine.

* * * * *